(12) United States Patent
Kapec et al.

(10) Patent No.: US 6,478,803 B1
(45) Date of Patent: Nov. 12, 2002

(54) DEVICE FOR DELIVERY OF SURGICAL MATERIALS

(75) Inventors: Jeffrey Kapec, Westport, CT (US);
Yukiko Naoi, New York, NY (US);
Allan Chochinov, New York, NY (US);
Kazuna Tanaka, Cos Cob, CT (US);
Sara McKenzie, Sherborn, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/574,811

(22) Filed: May 19, 2000

(51) Int. Cl.⁷ .................................................. A61B 17/08
(52) U.S. Cl. ....................................................... 606/151
(58) Field of Search ........................... 606/151; 604/13; 128/878

(56) References Cited

U.S. PATENT DOCUMENTS

| | | | |
|---|---|---|---|
| 5,263,927 A | | 11/1993 | Shlain ........................... 604/13 |
| 5,263,969 A | | 11/1993 | Phillips ........................ 606/213 |
| 5,304,187 A | * | 4/1994 | Green et al. ................. 606/151 |
| 5,350,387 A | | 9/1994 | Semm ........................... 606/151 |
| 5,354,292 A | * | 10/1994 | Braeuer et al. ................. 606/1 |
| 5,370,650 A | * | 12/1994 | Tovey et al. ................. 606/151 |
| 5,464,403 A | * | 11/1995 | Kieturakis et al. .............. 606/1 |
| 5,503,623 A | * | 4/1996 | Tilton, Jr. ...................... 604/13 |
| 5,766,157 A | | 6/1998 | Tilton, Jr. .................... 604/264 |
| 5,766,218 A | * | 6/1998 | Arnott ......................... 606/151 |
| 5,791,352 A | * | 8/1998 | Reich et al. ................. 128/898 |
| 5,797,899 A | | 8/1998 | Tilton, Jr. ........................ 606/1 |
| 5,906,997 A | | 5/1999 | Schwartz et al. ........... 514/781 |
| 5,919,184 A | | 7/1999 | Tilton, Jr. |
| 5,957,939 A | * | 9/1999 | Heaven et al. .............. 606/151 |

FOREIGN PATENT DOCUMENTS

WO    WO 97/36622    10/1997

* cited by examiner

Primary Examiner—Peter Nerbun
Assistant Examiner—Katherine Moran
(74) Attorney, Agent, or Firm—Richard D. Allison; Thomas J. DesRosier

(57) ABSTRACT

The present invention provides a novel apparatus for delivering a surgical material to a target site within a body cavity. The apparatus is characterized in part by a rod-like member to which a support carrier and a separator layer are attached at a distal end thereof for securing the surgical material therebetween, and an introducer tube for insertion into the body cavity. In certain preferred embodiments of the present invention, the rod-like member is configured for axial flexibility at a distal end thereof. Methods also are disclosed for applying the surgical material to the target site using the apparatus of the present invention.

34 Claims, 3 Drawing Sheets

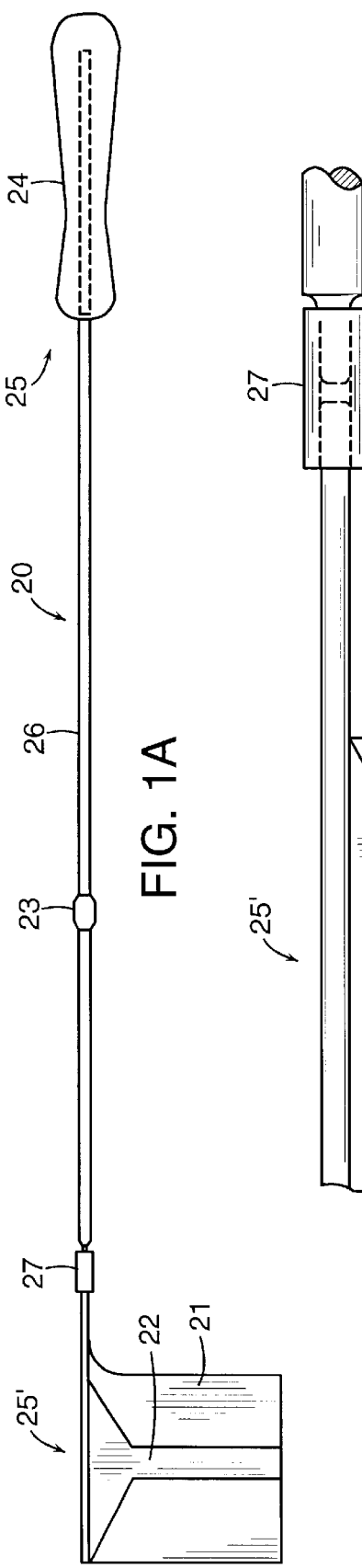
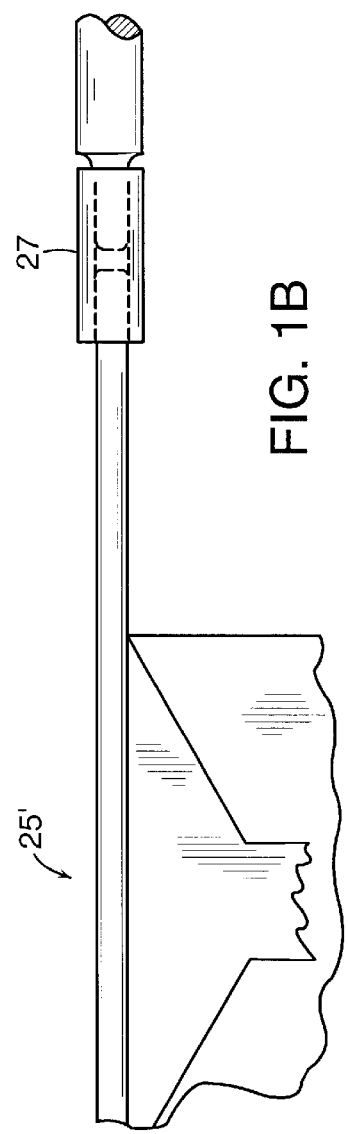
FIG. 1A
FIG. 1B
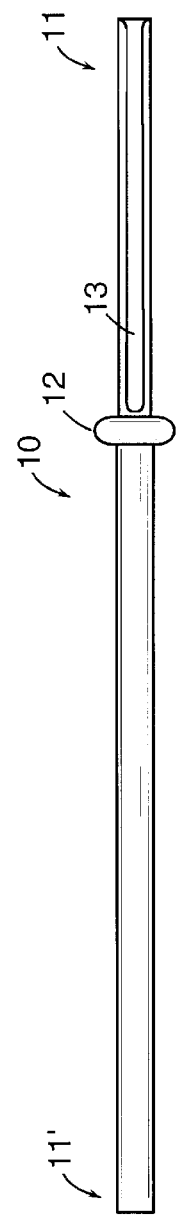
FIG. 2

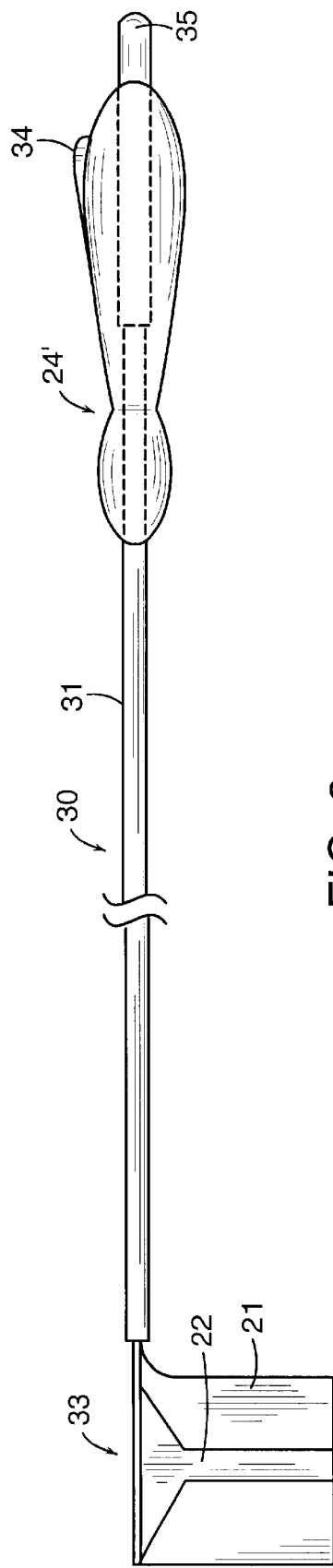
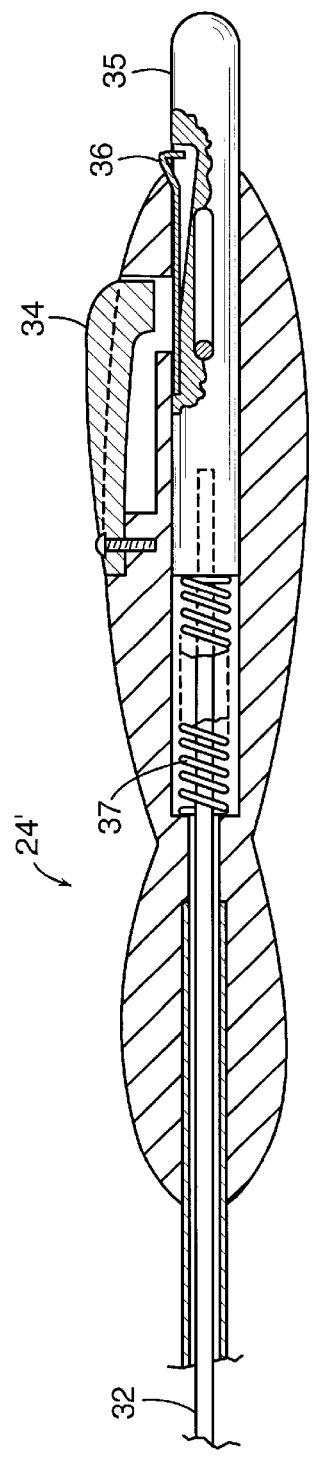
FIG. 3
FIG. 4

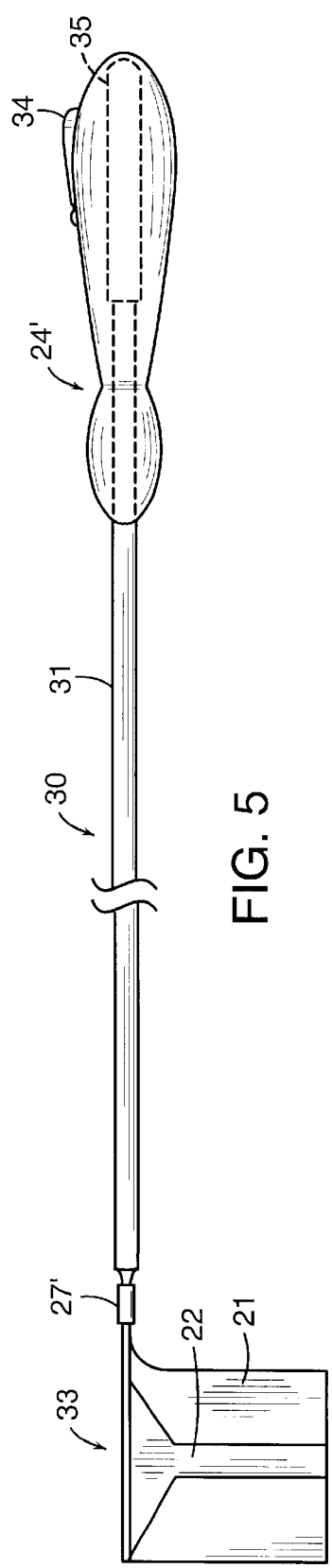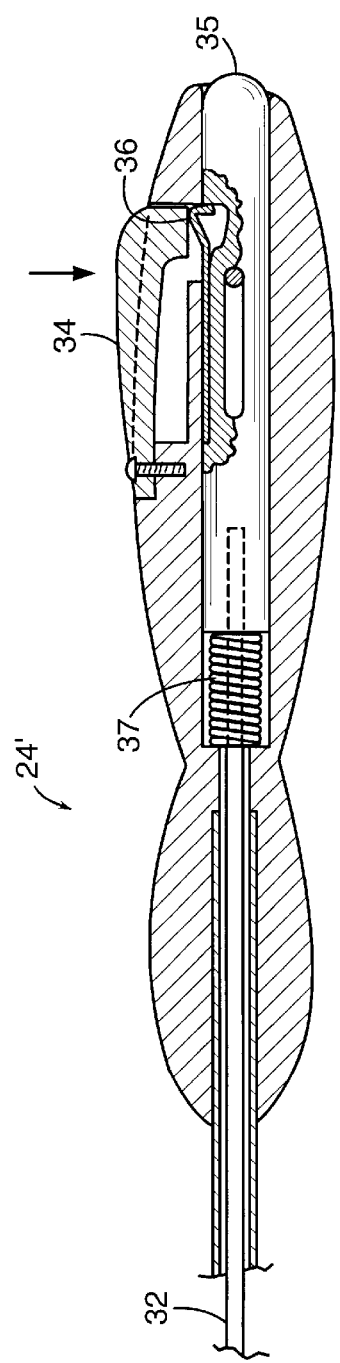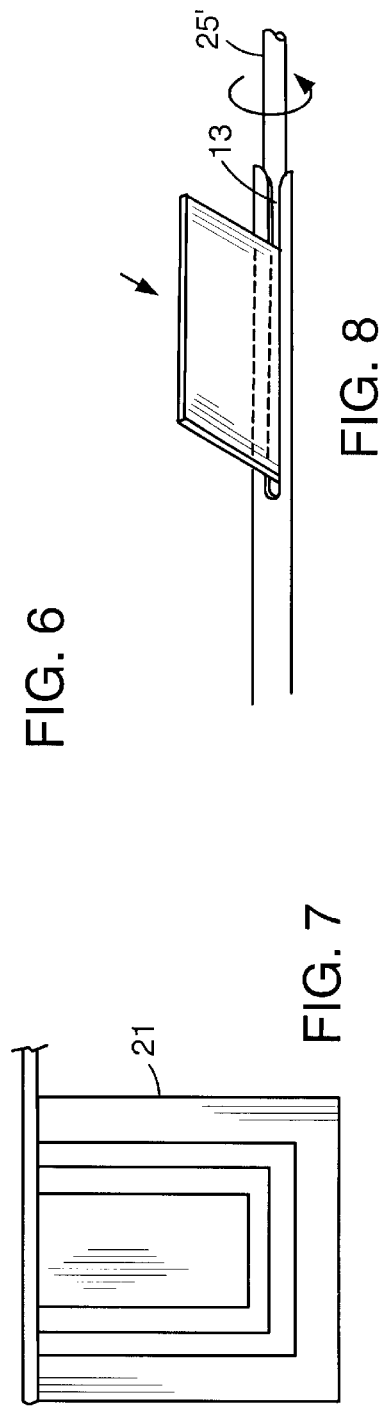
FIG. 5
FIG. 6
FIG. 7
FIG. 8

DEVICE FOR DELIVERY OF SURGICAL MATERIALS

BACKGROUND OF THE INVENTION

1. Field of the Invention

The present invention relates to an apparatus and methods for application of a surgical material to a target site within a body cavity. The apparatus and methods of the present invention are suitable for use in laparoscopic and endoscopic surgical procedures, as well as open-incision type procedures.

2. Background

Surgical prosthetic materials are used with a wide variety of surgical procedures. For example, prosthetic materials are often associated with hernia repair. Hernias are abnormal protrusions of an organ or other body structure through a defect or natural opening in a covering membrane, muscle or bone. Hernia repair typically involves replacement of the protruding tissue and repair or reconfiguration of the opening from which it protruded.

Surgical prostheses used in hernia repair and other procedures may include meshor gauze-like materials, which support the repaired hernia or other body structures, and/or anti-adhesion barriers, which are often placed between organs or tissues having different structures. Anti-adhesion barrier products are known to prevent the formation of adhesions between internal organs and/or the abdominal wall. Proper placement of such surgical prostheses is sometimes difficult, particularly where laparoscopic and endoscopic surgical procedures are utilized.

Laparoscopic and endoscopic surgical procedures offer significant advantages relative to conventional surgical procedures, and can often avoid the risks associated with such conventional procedures, e.g., bleeding, infection, and damage to organs, nerves and blood vessels.

In laparoscopic procedures, surgery is performed in the interior of the abdomen through narrow tubes inserted therein. Similarly, in endoscopic procedures, surgery is performed in any hollow cavity of the body through narrow endoscopic tubes inserted through small entrance wounds in the skin.

Since only small diameter incisions are required in laparoscopic and endoscopic procedures, trauma to the body (e.g., to the abdominal wall) is minimized, and the time required for healing and post-operative care is significantly shortened.

A number of devices have been developed for use in laparoscopic, endoscopic and open-incision delivery of surgical materials.

One such device is described in U.S. Pat. No. 5,503,623. The methods disclosed in this patent generally comprise grasping and furling a sheet of surgical material into a roll about a delivery tube, back-loading the delivery tube into an inserter sheath, then inserting the device into the abdomen for deploying and articulating the sheet within the abdomen. Placement of the sheet is facilitated by mechanical articulation of a grasping element.

Another device is described in U.S. Pat. No. 5,350,387. This device also is reported as being suitable for application of an adhesion prophylaxis, particularly a film-like material for use in endoscopic surgery. The apparatus disclosed includes a cylindrical application sleeve and a rod-like film carrier. An elongated reception area, e.g., a slot or clamping device, is provided at the forward end of the instrument for receiving the film. The film is frictionally engaged or grasped within the slot by roughened, opposing bearing surfaces and the adhesion prophylaxis is then wound about the film carrier for subsequent application within the body cavity. Other instruments, introduced by one or more separate trocars or cannulas, facilitate unwinding of the film.

These types of devices present certain limitations, particularly when they are used in laparoscopic and endoscopic procedures. For example, these devices are not suitable for use with most hygroscopic surgical materials; that is, those materials which absorb moisture from the air. Once hygroscopic materials become dampened (which is inevitable upon entry into a body cavity), they tend to become difficult to handle. Additionally, when folded, furled or wound about some type of inserter instrument (which is necessary in laparoscopic and endoscopic procedures), the surgical material may adhere to itself. In this case, unfolding or unwinding of the surgical material is very difficult, if not impossible. Thus, application of the particular surgical material to the target body tissue also becomes very difficult.

Another device for the endoscopic delivery of surgical elements is described in U.S. Pat. No. 5,304,187. The device described in that patent is reported as being particularly useful in the repair of herniated body tissue. Using that device, the surgical element is received through a longitudinal slot in an outer wall of a tubular member described as a housing means. Within the housing means, the element is grasped by a retainer means, then wound into a roll about the retainer means and maintained within the housing means. In preferred embodiments, the retainer means is described as a rod having two opposing convex members at its distal end. Upon entry into the body cavity, the device is positioned adjacent to the target body tissue, and the rolled surgical element is deployed, positioned and secured (e.g., with sutures, clips, staples, etc.) to the body tissue.

That device also is unsuitable for delivery of many hygroscopic surgical materials for the same reasons noted previously. Additionally, the device disclosed in that patent is particularly suited for delivery of a relatively stiff hernia repair material. Delivery of a thin, limp sheet of surgical material, e.g., a hygroscopic anti-adhesion product, would be very difficult, if not impossible, using such a device.

There remains a need for an improved apparatus for laparoscopic and endoscopic delivery of a wide variety of surgical materials to target sites within the body cavity. It would be highly desirable to develop an apparatus for laparoscopic, endoscopic, as well as open-incision delivery of such materials that could be used even for application of thin, limp, hygroscopic surgical materials. Further, it would be highly desirable to develop an apparatus for laparoscopic, endoscopic and open incision application of such materials that would not require the use of mechanical articulation in order to effectively position the surgical material at the target site, and that would not require insertion of additional instruments into the abdomen for articulation and securement of the material with respect to the target sites within the body cavity.

SUMMARY OF THE INVENTION

A central object of the present invention is to provide an apparatus suitable for use in a variety of surgical procedures, including laparoscopic, endoscopic and open incision surgical procedures, for application of a surgical material (e.g., a sheet, film, mesh or gauze) to a target site within a body cavity.

Though the apparatus of the present invention may be used for a wide variety of surgical materials, it is particularly well suited for the application of hygroscopic anti-adhesion products. Examples of such products include Seprafilm® manufactured by Genzyme Corporation and Interceed® manufactured by Johnson and Johnson.

Preferred anti-adhesion products have surfaces with very low coefficients of friction, especially when wetted, so that placement of the material between adjacent tissues will prevent adhesions from forming between the tissues and will allow some relative movement between the tissues without causing substantial tissue damage.

Such materials are typically in the form of dimensionally stable films that are easy to handle when in dry form. Further, such materials are non-adhesive, and preferred materials, such as Seprafilm®, will not cling to themselves or to adjacent surfaces when in dry form. However, preferred materials also are hygroscopic; that is, they absorb moisture from the air. Once hygroscopic material becomes damp or wet, it becomes difficult to handle. More specifically, when the surface of such material becomes wetted, the film has a tendency to cling to itself, to tissue, anatomical structures and various other materials, e.g., metal and plastics.

Because of these distinctive physical properties, devices of the prior art that are presently used in laparoscopic and endoscopic procedures to apply surgical materials are not suitable for use with preferred materials, such as Seprafilm® and other materials having similar physical properties.

The apparatus of the present invention generally comprises an introducer tube and a rod-like member comprising an elongated main portion having a distal portion connected thereto, to which a support carrier and a separator layer are attached. The rod-like member loosely resembles a flagpole, with its support carrier and separator layer corresponding to the flag portion.

Using the apparatus of the present invention, the surgical material is placed between the support carrier and the separator layer and then furled about the distal portion of the rod-like member. The furled surgical material is then typically wetted and inserted into the introducer tube at its proximal end.

The apparatus is introduced into the body cavity through a trocar, cannula or an open incision and moved into proximity of the target site, e.g., a certain body tissue. The rod-like member is first extended beyond the distal end of the introducer tube into the body cavity. Typically, the furled surgical material unfurls naturally once extended beyond the end of the introducer tube. If necessary, because of the confines of the body cavity, unfurling can be carried out or completed by simple, manual rotation of the rod-like member.

The surgical material is then placed directly on the target site with the separator layer facing downward. Upon contact, the surgical material typically adheres to moistened body tissue. The rod-like member is simply pulled away from the target site using a wiping action, thereby transferring the surgical material from the applicator to the desired body tissue. The ease of transfer is due in part to the physical properties of the surgical material. For example, Seprafilm® in wet form has a greater affinity for the body tissue than for the support carrier and separator layer of the rod-like member.

The use of an irrigator may be employed to accelerate and/or enhance the transfer of the surgical material to the target site. For example, once the surgical material has been placed on the target site, the corners of the support carrier may be dabbed with irrigation fluids using an irrigator.

In a particularly preferred embodiment of the present invention, the proximal end of the introducer tube comprises an open, slotted area on a portion of the outer wall thereof. This open area may be used to support the distal portion of the rod-like member during furling to produce an even, tightly furled surgical material located between the support carrier and separator layer. The furled surgical material can then easily be inserted into the introducer tube for subsequent application within the body cavity.

In another embodiment of the present invention, the proximal end of the introducer tube is flared to facilitate insertion of the rod-like member with its furled surgical material into the introducer tube.

In preferred embodiments of the present invention, the length of the rod-like member exceeds that of the introducer tube. This feature allows the surgeon to control the rod-like member from a position external to the body cavity, and permits extension of the rod-like member beyond the distal end of the introducer tube for delivery of the surgical material to the target site.

The diameter of the rod-like member is tailored to permit facile insertion and movement with respect to the introducer tube. In preferred embodiments of the present invention, the rod-like member has a reduced diameter at its distal end to accommodate the surgical material furled thereabout.

Preferably, the support carrier and separator layer comprise a woven screen media or mesh, e.g., media or mesh products available in a wide variety of weave configurations from Tetko, Inc., Sefar America, Inc. and Saati Tech. More preferably, the mesh comprises at least one of a nylon or polyolefin, e.g., polypropylene, polyester or teflon material. Most preferably, the mesh comprises a polyester material.

In particularly preferred embodiments of the present invention the support carrier is imprinted, e.g., with text, color or other design. Such an imprint aids in the visualization and placement of the surgical material during the application procedure.

The separator layer is preferably Y-shaped and its dimensions are tailored according to those of the support carrier.

In preferred embodiments of the present invention, the rod-like member further comprises an elongated handle adapted to control the movement of the rod-like member within the body cavity from a position external to the body cavity.

In an alternate preferred embodiment of the present invention, the rod-like member is configured for axial flexibility, e.g., it can bend in any axial direction. In this particular embodiment, the rod-like member comprises an outer tube surrounding an inner member having a distal portion to which the support carrier and separator layer are attached, the distal portion of the inner member being connected to the main portion by a flexible connector, and a device adapted to reversibly alter the flexibility of such distal portion. This design feature permits movement of the rod-like member in more than a single plane.

Preferably, the device for altering the flexibility of the rod-like member is easily accessible from a position external to the body cavity. In that way, the flexibility of the leading or distal end of the rod-like member can be adjusted without removing the apparatus from the body cavity.

In preferred embodiments of the present invention, the device comprises a control unit, e.g., a push-button assembly, located on the handle portion of the rod-like member. When the push-button is not depressed, the rod-like member operates in its semi-rigid form. Depressing the push-button of the control unit causes the actuation, e.g., extension, of the inner member such that at least a portion of the flexible connector is advanced beyond the distal end of the outer tube of the rod-like member rendering the leading end of the rod-like member highly flexible. The inner member and flexible connector may be retracted and extended as needed to reversibly alter the flexibility of the rod-like member.

Another object of this invention is to provide methods for using the apparatus of the present invention.

One preferred method of the present invention for delivering a surgical material to a target site within a body cavity comprises providing an apparatus in accordance with the present invention; placing the surgical material between the support carrier and separator layer of the rod-like member and furling thereabout; inserting the rod-like member into the proximal end of the introducer tube and inserting the apparatus into the body cavity, e.g., with the use of a trocar or cannula, or via an open incision; positioning the apparatus within proximity of the target site; extending the rod-like member beyond the distal end of the introducer tube and allowing the surgical material at least partially to unfurl; applying the surgical material to the target site; and withdrawing the apparatus from the body cavity.

The preferred methods of the present invention may also comprise wetting the furled surgical material with suitable irrigation fluids prior to inserting it into the introducer tube.

The preferred methods of the present invention may also comprise altering the flexibility of the leading or distal end of the rod-like member to facilitate positioning of the rod-like member in proximity to the target site.

The preferred methods of the present invention may also comprise providing a visual indicator, e.g., in the form of text, color or other design, on the support carrier of the rod-like member to assist in the placement and application of the surgical material.

The preferred methods of the present invention may further comprise irrigating the surgical material following placement on the target site to accelerate and/or enhance transfer of the surgical material from the support carrier and separator layer to the target site.

The foregoing and other objects, features and advantages of the invention will become better understood with reference to the following description and appended claims.

BRIEF DESCRIPTION OF THE DRAWINGS

FIGS. 1A and 1B are side views of the rod-like member in a preferred embodiment of the present invention.

FIG. 2 is a side view of the introducer tube in a preferred embodiment of the present invention.

FIG. 3 is a side view of an alternate embodiment of the rod-like member shown in FIG. 1 in its semi-rigid position.

FIG. 4 is a cross-sectional view of the elongated handle portion of the rod-like member of FIG. 3.

FIG. 5 is a side view of the rod-like member shown in FIG. 3 in its flexible position.

FIG. 6 is a cross-sectional view of the elongated handle portion of the rod-like member of FIG. 5.

FIG. 7 shows a support carrier comprising a visual indicator in a preferred embodiment of the present invention.

FIG. 8 shows the surgical material (located between the support carrier and support layer) being furled about the rod-like member using the slotted area of the introducer tube as a support in a preferred embodiment of the present invention.

DETAILED DESCRIPTION OF THE INVENTION

The apparatus and methods of the present invention may be used for the laparoscopic, endoscopic and open incision delivery of a wide variety of surgical materials. Such surgical materials may be in the form of a sheet, film, mesh or gauze, and may comprise a biologically resistant material and/or a bioresorbable material, e.g., a material that dissolves over a period of time and does not require subsequent removal.

The novel design of the present invention prevents the surgical material from clinging to itself or to unwanted, e.g., non-targeted, surfaces during the surgical procedure. Using the apparatus of the present invention, the surgeon may control application of the surgical material much more easily than in the devices of the prior art. Typically, no mechanical articulation is required to position or secure the surgical material to the target site.

Referring to FIGS. 1A, 1B and 2, an apparatus of the present invention is shown. The apparatus generally comprises two main components: an introducer tube 10 having a proximal end 11 and a distal end 11'; and a rod-like member 20 comprising an elongated main portion 26 to which a support carrier 21 and a separator layer 22 are attached at a distal portion thereof 25'. Connector 27 is used to connect the main portion 26 of the rod-like member 20 to the distal end thereof 25'. The rod-like member 20 loosely resembles a flagpole, with its support carrier 21 and separator layer 22 corresponding to the flag portion. (In accordance with conventional practice regarding medical devices, "proximal end" designates that end which is closest to the medical personnel manipulating the device, and "distal end" designates the opposite end that is placed within a patient.)

In preferred embodiments of the present invention, the rod-like member 20 further comprises an elongated handle 24 adapted to control the movement of the rod-like member 20 within the body cavity from a position external to the body cavity.

Laparoscopic and endoscopic procedures generally require insufflation of the surgical region, e.g., the abdomen. Therefore, in one preferred embodiment of the present invention, the introducer tube and rod-like member further comprise one or more bushing stops or cylindrical seals to prevent gases from entering or exiting the body through the incision.

Referring to FIG. 2, bushing stop 12 on the outer surface of the introducer tube 10 facilitates handling and contact between the introducer tube and the inner surface of the trocar or cannula during laparoscopic and endoscopic procedures. Further, bushing stop 12 prevents the introducer tube 10 from slipping through the trocar or cannula during such procedures.

Similarly, referring to FIG. 1A, cylindrical seal 23 on the outer surface of the rod-like member 20 facilitates its contact with the inner surface of the introducer tube 10 and blocks or prevents insufflation gas bypass.

Alternatively, the respective diameters of the introducer tube and rod-like member may be configured relative to the diameter of the trocar or cannula, such that only very small gaps are present between these instruments, e.g., less than about 0.002 inches, thereby obviating the need for such bushing stops and other seals.

The preferred embodiments of the present invention are further illustrated by the following description of the apparatus in a typical procedure.

The surgical material is first placed between the support carrier 21 and the separator layer 22 and then furled about the rod-like member 20 at its distal end 25'. The furled surgical material is then inserted into the introducer tube 10 at its proximal end 11. If desirable due to the properties of the surgical material, the furled surgical material may be wetted, at least partially, with a suitable irrigation fluid prior to insertion into the introducer tube in order to reduce the brittleness of the surgical material and to otherwise enhance the application procedure.

The apparatus of the present invention is introduced into the body cavity through a trocar, cannula or open incision and moved into proximity of the target site, e.g., a certain body tissue. The rod-like member 20 is extended beyond the distal end 11' of the introducer tube 10 into the body cavity. Typically, the furled surgical material unfurls naturally once extended beyond the distal end 11' of the introducer tube 10. If necessary, because of the confines of the body cavity, unfurling can be carried out or completed by simple, manual rotation of the rod-like member 20.

The surgical material is then placed directly on the target site with the separator layer 22 facing downward. The rod-like member 20 is gently pulled away from the target site using a wiping action, thereby transferring the surgical material from the applicator to the desired body tissue. The ease of transfer is due in part to the physical properties of the surgical material. For example, Seprafilm® in wet form has a greater affinity for the body tissue than for the support carrier and separator layer of the rod-like member.

An irrigator (not shown) may be employed to accelerate and/or enhance the transfer of the surgical material to the target site. For example, once the surgical material has been placed on the target site, the corners of the support carrier may be dabbed with irrigation fluid using an irrigator prior to pulling the applicator away from the target site.

Preferably the introducer tube 10 is made of stainless steel or like material. More preferably, the introducer tube 10 is a 5 gauge, 316 stainless steel tube having dimensions of about 8 inches to about 12 inches in length, most preferably about 10 inches in length, an outer diameter of about 0.15 to about 0.3 inches, most preferably about 0.218 inches, and a preferred inner diameter of about 0.2 inches (wall thickness of about 0.010 inches to about 0.020 inches).

In a particularly preferred embodiment of the present invention, the proximal end 11 of the introducer tube 10 comprises an open or slotted area 13. This particular embodiment is shown in FIG. 2. Open area 13 may be used to support the distal portion 25' of the rod-like member 20 during furling to produce an even, tightly furled surgical material located between the support carrier 21 and separator layer 22. The furled surgical material is typically wetted, at least partially, and then inserted into the introducer tube 10. (See, e.g., the illustration of FIG. 8.)

In such an embodiment, open area 13 is present on a portion of the wall of the introducer tube 10 and preferably has dimensions of about 3 inches to about 3½ inches in length, more preferably about 3¼ inches in length. Preferably, open area 13 has a circular cross-section shape with a diameter of about 0.1 inches, but many different shapes and configurations may be employed, if desired.

Though generally less preferred, in another embodiment of the present invention, the proximal end 11 of the introducer tube 10 is flared. The wider opening provided by the flared configuration facilitates insertion of the rod-like member 20 with its surgical material furled thereabout into the introducer tube 10.

Preferably, the main portion 26 of the rod-like member 20 is made of stainless steel or like material, while the distal portion 25' to which the support carrier and separator layer are attached is made from a polymer, e.g., polyvinyl chloride (PVC), polycarbonate or other suitable, non-reactive materials. Connector 27 is preferably made of flexible tubing and is used to connect the distal portion of the rod-like member to the main (stainless steel) portion. Such tubing may be made from a variety of materials as will be appreciated in by those skilled in the art, e.g., PVC or like material.

In preferred embodiments of the present invention, the overall length of the rod-like member 20 exceeds that of the introducer tube 10. This feature allows the surgeon to control the rod-like member from a position external to the body cavity and permits extension of the rod-like member beyond the distal end 11' of the introducer tube 10 for delivery of the surgical material to the target site.

The diameter of rod-like member 20 is tailored to permit facile movement when inserted into the introducer tube 10. In preferred embodiments of the present invention, the rod-like member 20 has a reduced diameter at its distal end 25' to accommodate the surgical material once furled thereabout and to facilitate insertion into the introducer tube 10.

In preferred embodiments of the present invention, the rod-like member 20 has dimensions of about 20 inches to about 21 inches in length inclusive of the handle portion. Preferably, elongated handle 24 has dimensions of about 4 inches in length.

Preferably, the support carrier 21 and separator layer 22 comprise a woven screen media or mesh, e.g., media or mesh products available in a wide variety of weave configurations from Tetko, Inc., Sefar America, Inc. and Saati Tech.

Preferably, mesh products used for the support carrier 21 and separator layer 22 comprise at least one of a nylon, polypropylene, polyester or teflon material. Even more preferably, the mesh comprises a polyester material having a weave configuration which includes a pore size range of about 80 microns to about 120 microns, an open area of about 40% to about 60% per square inch, and a thickness of about 50 microns to about 100 microns. Most preferably, the mesh comprises a polyester material having a weave configuration which includes a pore size of about 105 microns, an open area of about 50% per square inch, and a thickness of about 60 microns.

Interestingly, the reduced surface area of the mesh provides significant advantages over a solid sheet support carrier, especially when the apparatus is used for delivery and application of preferred materials. While the surface area and surface attraction of the mesh is sufficient to hold the material in place, even in wet form, it does not present too much friction so as to prevent or impair the transfer of the material from the support carrier and separator layer to the target site.

The dimensions of the support carrier 21 may vary in order to accommodate differing sizes of surgical materials. Preferably, the support carrier 21 is square shaped with sides of about 1½ to about 2 inches in length, more preferably about 1¾ inches in length.

In particularly preferred embodiments of the present invention, the support carrier 21 is imprinted, e.g., with text, color or other design. (See e.g., the illustration in FIG. 7) Such an imprint aids the attendant medical personnel in visualization and thus, placement of the surgical material during the application procedure.

The separator layer 22 is preferably Y-shaped and its dimensions are tailored according to those of the support carrier 21.

Referring now to FIGS. 3–6, an alternate preferred embodiment of the rod-like member of the present invention is shown. In this particular embodiment, the rod-like member 30 is configured for axial flexibility, e.g., it can bend in any axial direction. The rod-like member 30 comprises an outer tube 31 surrounding an inner member 32 having a distal portion to which the support carrier 21 and separator layer 22 are attached, the distal portion 33 of the inner member 32 (analogous to 25' of rod-like member 20 above) being connected to the main portion of the inner member 32 by a flexible connector 27', and a device adapted to reversibly alter the flexibility of such distal portion.

This novel design feature permits movement of the rod-like member in more than a single plane. In that way, the apparatus of the present invention is particularly useful when maneuvering the rod-like member within the body cavity to position the surgical material in close proximity of the target site. The universal flexibility of the rod-like member in this embodiment facilitates effective application of the surgical material even in the narrow confines of the body cavity.

Preferably, the outer tube 31 and the main portion of the inner member 32 are made of stainless steel or other like material. The distal portion 33 of the inner member 32 to which the support carrier 21 and separator layer 22 are attached is made from a polymer, e.g., PVC, polycarbonate or other suitable, non-reactive materials.

Referring with particularity to FIG. 5, flexible connector 27' is shown connecting the distal portion 33 of the inner member 32 to the main (stainless steel) portion. Such a connector may be made from a variety of materials as will be appreciated in by those skilled in the art, e.g. PVC or like material.

Preferably, the device for altering the flexibility of the rod-like member 30 is easily accessible from a position external to the body cavity. In that way, the flexibility of the leading or distal end 33 of the rod-like member 30 can be adjusted without removing the apparatus from the body cavity.

Preferably, the device comprises a control unit, e.g., a push-button assembly, located on the handle portion 24' of the rod-like member 30. Such an assembly comprises push-button release 34, push-button 35, pin 36 and spring 37.

Referring with particularity to FIGS. 3 and 4, when the push-button 35 is not depressed, the rod-like member 30 operates in a semi-rigid form. Referring now to FIGS. 5 and 6, depressing the push-button 35 of the control unit causes the actuation, e.g., extension, of the inner member 32 such that at least a portion of the flexible connector 27' is advanced beyond the distal end of the outer tube 31 of the rod-like member 30 rendering the leading end of the rod-like member highly flexible. The inner member 32 and flexible connector 27' may be retracted and extended as needed to reversibly alter the flexibility of the rod-like member 30.

Another object of this invention is to provide methods for using the apparatus of the present invention.

One preferred method of the present invention for delivering a surgical material to a target site within a body cavity comprises providing an apparatus in accordance with the present invention, placing the surgical material between the support carrier and separator layer of the rod-like member and furling thereabout; inserting the rod-like member into the proximal end of the introducer tube and inserting the apparatus into the body cavity, e.g., with the use of a trocar or cannula, or via an open incision; positioning the apparatus within proximity of the target site; extending the rod-like member beyond the distal end of the introducer tube and allowing the surgical material to unfurl; applying the surgical material to the target site; and withdrawing the apparatus from the body cavity.

The preferred methods of the present invention also may comprise wetting the furled surgical material with suitable irrigation fluids prior to inserting it into the introducer tube with suitable irrigation fluids. Wetting of the furled surgical material may be desirable due to the properties of the surgical material in order to reduce the brittleness of the surgical material and to otherwise enhance the application procedure.

The preferred methods of the present invention may also comprise altering the flexibility of the leading or distal end of the rod-like member to facilitate positioning of the rod-like member in proximity to the target site. As described above, using a suitable device, e.g., push-button assembly, the inner member of the rod-like member may be actuated, e.g., extended, such that at least a portion of the flexible connector is advanced beyond the distal end of the outer tube. In this way, the leading end of the rod-like member becomes highly flexible. The inner member and its flexible connector may be retracted and extended as needed to reversibly alter the flexibility of the rod-like member during the procedure.

The preferred methods of the present invention may also comprise providing a visual indicator, e.g., in the form of text, color or other design, on the support carrier of the rod-like member to assist in the placement or application of the surgical material at the desired target site.

The preferred methods of the present invention may further comprise irrigating the surgical material following placement on the target site to accelerate and/or enhance transfer of the surgical material from the support carrier and separator layer to the target site.

The terms and expressions which have been employed herein are used as terms of description and not of limitation. There is no intent, in the use of such terms and expressions, of excluding any of the equivalents of the features shown and described or portions thereof, but it is recognized that various modifications are possible within the scope of the invention claimed.

What is claimed is:

1. An apparatus for delivery of a surgical material into a body cavity comprising:
    an introducer tube having a proximal end and a distal end;
    a rod-like member comprising an elongated main portion having a distal portion connected thereto, to which a support carrier and a separator layer are attached for securing the surgical material therebetween, wherein the rod-like member is capable of insertion into the proximal end of the introducer tube and extension beyond the distal end of the introducer tube; and
    a flexibility altering device on the main portion of the rod-like member to allow an adjustable connection between the distal portion and the rod-like member between rigid and flexible configurations.

2. The apparatus of claim 1, wherein the proximal end of the introducer tube comprises a slotted area on an outer wall thereof.

3. The apparatus of claim 1, wherein the proximal end of the introducer tube is flared.

4. The apparatus of claim 1 further including a surgical material thereon and wherein the surgical material is an anti-adhesion barrier that is supported by the support carrier and separator layer that are formed of a mesh material.

5. An apparatus for delivery of a surgical material into a body cavity comprising:

an introducer tube having a proximal end and a distal end;

a rod-like member comprising an elongated main portion having a distal portion connected thereto, to which a support carrier and a separator layer are attached for securing the surgical material therebetween, wherein the rod-like member is capable of insertion into the proximal end of the introducer tube and extension beyond the distal end of the introducer tube; and wherein the separator layer is Y-shaped.

6. An apparatus for delivery of a surgical material into a body cavity comprising:

an introducer tube having a proximal end and a distal end;

a rod-like member comprising an elongated main portion having a distal portion connected thereto, to which a support carrier and a separator layer are attached for securing the surgical material therebetween, wherein the rod-like member is capable of insertion into the proximal end of the introducer tube and extension beyond the distal end of the introducer tube; and wherein the support carrier is imprinted with text, color or other design which indicates the orientation of the support carrier.

7. An apparatus for delivery of a surgical material into a body cavity comprising:

an introducer tube having a proximal end and a distal end;

a rod-like member comprising an elongated main portion having a distal portion connected thereto, to which a support carrier and a separator layer are attached for securing the surgical material therebetween, wherein the rod-like member is capable of insertion into the proximal end of the introducer tube and extension beyond the distal end of the introducer tube; and wherein the support carrier and separator layer comprise a mesh material.

8. The apparatus of claim 7, wherein the mesh comprises a polyester material.

9. An apparatus for delivery of a surgical material into a body cavity comprising:

an introducer tube having a proximal end and a distal end;

a rod-like member comprising an elongated handle adapted to control the movement of the rod-like member from a position external to the body cavity, an outer tube surrounding an inner member, said inner member having a distal portion flexibly connected thereto, to which a support carrier and a separator layer are attached, and wherein the rod-like member is capable of insertion into the proximal end of the introducer tube and extension beyond the distal end of the introducer tube into the body cavity; and wherein at least one of the support carrier and separator layer include an indicator thereon that indicates the orientation of at least one of the support carrier and the separator layer in the body cavity.

10. The apparatus of claim 9, wherein the proximal end of the introducer tube comprises a slotted area on an outer wall thereof.

11. The apparatus of claim 9 further including a surgical material thereon and wherein the surgical material is an anti-adhesion barrier that is supported by the support carrier and separator layer that are formed of a mesh material.

12. An apparatus for delivery of a surgical material into a body cavity comprising:

an introducer tube having a proximal end and a distal end;

a rod-like member comprising an elongated handle adapted to control the movement of the rod-like member from a position external to the body cavity, an outer tube surrounding an inner member, said inner member having a distal portion flexibly connected thereto, to which a support carrier and a separator layer are attached, and wherein the rod-like member is capable of insertion into the proximal end of the introducer tube and extension beyond the distal end of the introducer tube into the body cavity; and wherein the rod-like member further comprises a device adapted to reversibly alter the flexibility of a distal portion of the rod-like member.

13. The apparatus of claim 12, wherein the device adapted for reversibly altering the flexibility of the rod-like member is positioned such that the rod-like member operates in a semi-rigid configuration relative to the distal portion thereof.

14. The apparatus of claim 12, wherein the device adapted for reversibly altering the flexibility of the rod-like member is positioned such that the rod-like member operates in a flexible configuration relative to the distal portion thereof.

15. The apparatus of claim 12, wherein the distal portion of the rod-like member is operably actuatable or flexible in any axial direction.

16. An apparatus for delivery of a surgical material into a body cavity comprising:

an introducer tube having a proximal end and a distal end;

a rod-like member comprising an elongated handle adapted to control the movement of the rod-like member from a position external to the body cavity, an outer tube surrounding an inner member, said inner member having a distal portion flexibly connected thereto, to which a support carrier and a separator layer are attached, and wherein the rod-like member is capable of insertion into the proximal end of the introducer tube and extension beyond the distal end of the introducer tube into the body cavity;

wherein the rod-like member further comprises a device adapted to reversibly alter the flexibility of a distal portion of the rod-like member; and wherein the flexibility altering device is operated by a push-button assembly.

17. An apparatus for delivery of a surgical material into a body cavity comprising:

an introducer tube having a proximal end and a distal end;

a rod-like member comprising an elongated handle adapted to control the movement of the rod-like member from a position external to the body cavity, an outer tube surrounding an inner member, said inner member having a distal portion flexibly connected thereto, to which a support carrier and a separator layer are attached, and wherein the rod-like member is capable of insertion into the proximal end of the introducer tube and extension beyond the distal end of the introducer tube into the body cavity; and wherein the separator layer is Y-shaped.

18. An apparatus for delivery of a surgical material into a body cavity comprising:

an introducer tube having a proximal end and a distal end; and a rod-like member comprising an elongated handle adapted to control the movement of the rod-like member from a position external to the body cavity, an outer tube surrounding an inner member, said inner member having a distal portion flexibly connected thereto, to which a support carrier and a separator layer are attached, and wherein the rod-like member is capable of insertion into the proximal end of the introducer tube and extension beyond the distal end of the introducer tube into the body cavity; and wherein the support carrier and separator layer comprise a mesh material.

19. The apparatus of claim 18, wherein the mesh comprises a polyester material.

20. An apparatus for delivery of a surgical material into a body cavity comprising:

an elongate introducer tube having a proximal end portion and a distal end portion;

a rod-like member having an elongated main portion with a distal portion connected thereto and wherein the distal portion includes a support carrier and a separator layer connected thereto for securing the surgical material therebetween and wherein the rod-like member is capable of insertion into the proximal end portion of the introducer tube and extending beyond the distal end portion of the introducer tube; and wherein the connection between the main portion and the distal portion of the rod-like member is adjustable between a rigid connection and a flexible connection upon actuation of a member on the rod-like member.

21. An apparatus for delivery of a surgical material into a body cavity comprising:

an elongate introducer tube having a proximal end portion and a distal end portion;

a rod-like member having an elongated main portion with a distal portion connected thereto and wherein the distal portion includes a support carrier and a separator layer connected thereto for securing the surgical material therebetween and wherein the rod-like member is capable of insertion into the proximal end portion of the introducer tube and extending beyond the distal end portion of the introducer tube; and wherein the support carrier includes an imprinted surface thereon to indicate the orientation of the support carrier in the cavity.

22. A method of delivering a surgical material to a target site within a body cavity comprising:

providing an apparatus comprising an introducer tube having a proximal end and a distal end, and a rod-like member comprising an elongated main portion having a distal portion connected thereto, to which a support carrier and a separator layer are attached for securing the surgical material therebetween;

placing the surgical material between the support carrier and separator layer of the rod-like member and furling the support carrier thereabout;

inserting the rod-like member into the proximal end of the introducer tube and inserting the apparatus into the body cavity;

positioning the apparatus within proximity of the target site;

extending the rod-like member beyond the distal end of the introducer tube;

applying the surgical material to the target site in accordance with the desired orientation thereof as indicated by a visual indicator on one or both of the support carrier and the separator layer; and withdrawing the apparatus from the body cavity.

23. The method of claim 22, further comprising wetting the furled surgical material with suitable irrigation fluids prior to inserting the rod-like member into the introducer tube.

24. The method of claim 22, wherein applying the surgical material to the target site comprises allowing the surgical material to unfurl while still located between the support carrier and separator layer, placing the surgical material on the target site, allowing the surgical material to adhere to the target site, and withdrawing the support carrier and separator layer from the target site.

25. A method of delivering a surgical material to a target site within a body cavity comprising:

providing an apparatus comprising an introducer tube having a proximal end and a distal end, and a rod-like member comprising an elongated main portion having a distal portion connected thereto, to which a support carrier and a separator layer are attached for securing the surgical material therebetween;

placing the surgical material between the support carrier and separator layer of the rod-like member and furling the support carrier thereabout;

inserting the rod-like member into the proximal end of the introducer tube and inserting the apparatus into the body cavity;

positioning the apparatus within proximity of the target site;

extending the rod-like member beyond the distal end of the introducer tube;

applying the surgical material to the target site;

withdrawing the apparatus from the body cavity; and further including the step of providing a visual indicator for indicating the orientation of the support carrier of the rod-like member in the body cavity to assist in applying the surgical material to the target site.

26. A method of delivering a surgical material to a target site within a body cavity comprising:

providing an apparatus comprising an introducer tube having a proximal end and a distal end, and a rod-like member comprising an elongated main portion having a distal portion connected thereto, to which a support carrier and a separator layer are attached for securing the surgical material therebetween;

placing the surgical material between the support carrier and separator layer of the rod-like member and furling the support carrier thereabout;

inserting the rod-like member into the proximal end of the introducer tube and inserting the apparatus into the body cavity;

positioning the apparatus within proximity of the target site;

extending the rod-like member beyond the distal end of the introducer tube;

applying the surgical material to the target site withdrawing the apparatus from the body cavity; and wherein a visual indicator comprising text, color or other design is provided to indicate the orientation of the support carrier relative to the separator layer in the body cavity.

27. A method of delivering a surgical material to a target site within a body cavity comprising:

providing an apparatus comprising an introducer tube having a proximal end and a distal end, and a rod-like member comprising an outer tube surrounding an elongated inner member and a handle at a proximal end thereof, said inner member having a distal portion attached thereto by an adjustable connector that is adjustable between flexible and rigid configurations, to which a support carrier and a separator layer are attached;

placing the surgical material between the support carrier and separator layer of the rod-like member and furling the support carrier thereabout;

inserting the rod-like member into the proximal end of the introducer tube and inserting the apparatus into the body cavity;

positioning the apparatus within proximity of the target site;

extending the rod-like member beyond the distal end of the introducer tube;

adjusting g the flexibility of the adjustable connector;

applying the surgical material to the target site; and withdrawing the apparatus from the body cavity.

28. The method of claim 27, further comprising wetting the furled surgical material with suitable irrigation fluids prior to inserting the rod-like member into the introducer tube.

29. The method of claim 27, further comprising altering the flexibility of the connection between the distal end and the rod-like member to a flexible connection to facilitate positioning the rod-like member within proximity of the target site.

30. A method of delivering a surgical material to a target site within a body cavity comprising:

providing an apparatus comprising an introducer tube having a proximal end and a distal end, and a rod-like member comprising an outer tube surrounding an elongated inner member and a handle at a proximal end thereof, said inner member having a distal portion attached thereto by a flexible connector, to which a support carrier and a separator layer are attached;

placing the surgical material between the support carrier and separator layer of the rod-like member and furling the support carrier thereabout;

inserting the rod-like member into the proximal end of the introducer tube and inserting the apparatus into the body cavity;

positioning the apparatus within proximity of the target site;

extending the rod-like member beyond the distal end of the introducer tube;

applying the surgical material to the target site;

withdrawing the apparatus from the body cavity; and further comprising providing a visual indicator on the support carrier of the rod-like member to provide an indication of the orientation of the support carrier in the body cavity to assist in applying the surgical material to the target site.

31. A method of delivering a surgical material to a target site within a body cavity comprising:

providing an apparatus comprising an introducer tube having a proximal end and a distal end, and a rod-like member comprising an outer tube surrounding an elongated inner member and a handle at a proximal end thereof, said inner member having a distal portion attached thereto by a flexible connector, to which a support carrier and a separator layer are attached;

placing the surgical material between the support carrier and separator layer of the rod-like member and furling the support carrier thereabout;

inserting the rod-like member into the proximal end of the introducer tube and inserting the apparatus into the body cavity;

positioning the apparatus within proximity of the target site;

extending the rod-like member beyond the distal end of the introducer tube;

applying the surgical material to the target site;

withdrawing the apparatus from the body cavity; and wherein a visual indicator is provided that comprises text, color or other design and is provided on the support carrier or separator layer to provide an indication of the orientation thereof in the body cavity.

32. The method of claim 31, further comprising irrigating the surgical material to facilitate transfer of the surgical material from the support carrier and separator layer to the target site.

33. A method of delivering a surgical material to a target site within a body cavity comprising:

providing an apparatus comprising an elongate rod-like member having an elongated main portion with a distal portion connected thereto and wherein the distal portion includes a support carrier and a separator layer connected thereto for securing the surgical material therebetween;

placing the surgical material between the support carrier and separator layer of the rod-like member;

furling the support carrier having the surgical material thereon about the distal portion of the rod-like member;

inserting the rod-like member into the proximal end portion of an introducer tube and extending a portion of the rod-like member beyond the distal end portion of the introducer tube and into the body cavity;

positioning the apparatus within proximity of the target site;

unfurling the support carrier;

adjusting the rigidity of the connection between the main portion and distal portion of the rod-like member by actuating a member on the rod-like member; and applying the surgical material to the target site and withdrawing the apparatus from the body cavity.

34. A method of delivering a surgical material to a target site within a body cavity comprising:

providing an apparatus comprising an elongate rod-like member having an elongated main portion with a distal portion connected thereto and wherein the distal portion includes a support carrier and a separator layer connected thereto for securing the surgical material therebetween;

placing the surgical material between the support carrier and separator layer of the rod-like member;

furling the support carrier having the surgical material thereon about the distal portion of the rod-like member;

inserting the rod-like member into the proximal end portion of an introducer tube and extending a portion of the rod-like member beyond the distal end portion of the introducer tube and into the body cavity;

positioning the apparatus within proximity of the target site;

unfurling the support carrier and orienting the surgical material in accordance with a visual indicator on the support carrier; and applying the surgical material to the target site and withdrawing the apparatus from the body cavity.

* * * * *